(12) United States Patent
Dadachova et al.

(10) Patent No.: US 7,402,385 B2
(45) Date of Patent: Jul. 22, 2008

(54) RADIOLABELED ANTIBODIES FOR TREATMENT OF TUMORS

(75) Inventors: Ekaterina Dadachova, Mahopac, NY (US); Joshua D. Nosanchuk, Upper Saddle River, NJ (US); Arturo Casadevall, Pelham, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 79 days.

(21) Appl. No.: 10/775,869

(22) Filed: Feb. 10, 2004

(65) Prior Publication Data

US 2004/0156780 A1 Aug. 12, 2004

Related U.S. Application Data

(60) Provisional application No. 60/446,684, filed on Feb. 11, 2003.

(51) Int. Cl.
*A61K 39/00* (2006.01)
*A61K 39/396* (2006.01)

(52) U.S. Cl. .................. 435/6; 424/1.49; 424/130.1; 424/155.1

(58) Field of Classification Search .................. 424/1.49
See application file for complete search history.

(56) References Cited

U.S. PATENT DOCUMENTS

| | | | |
|---|---|---|---|
| 4,444,744 A | | 4/1984 | Goldenberg |
| 4,460,561 A | * | 7/1984 | Goldenberg ............... 424/1.49 |
| 5,047,227 A | * | 9/1991 | Rodwell et al. ............ 424/1.49 |
| 5,102,990 A | | 4/1992 | Rhodes |
| 5,332,567 A | | 7/1994 | Goldenberg |
| 6,077,499 A | | 6/2000 | Griffiths et al. |
| 6,319,500 B1 | | 11/2001 | Goldenberg |
| 6,342,221 B1 | * | 1/2002 | Thorpe et al. ............. 424/178.1 |
| 6,395,276 B1 | | 5/2002 | Rybak et al. |
| 6,458,933 B1 | | 10/2002 | Hansen |
| 6,548,275 B2 | | 4/2003 | Goldenberg |
| 6,653,104 B2 | | 11/2003 | Goldenberg |
| 6,667,024 B1 | | 12/2003 | Goldenberg et al. |
| 2003/0198595 A1 | | 10/2003 | Goldenberg et al. |
| 2006/0039858 A1 | | 2/2006 | Dadachova et al. |

OTHER PUBLICATIONS

Mason et al. (Cancer Research 1954; 14; 648-650).*
Wilder et al. (J. Clin. Oncol. 1996; 14: 1383-1400).*
Erdi et al. (Phys. Med. Biol. 1996; 41: 2009-2026).*
Chatel et al. (Eur. J. Nucl. Med. 1992; 19: 205-213).*
[Fundamental Immunology 242 (William E. Paul, M.D. ed., 3rd ed. 1993)]—292-295.*
Wilder et al. (J. Clin. Oncol. 1996; 14: 1383-1400).*
Erdi et al. (Phys. Med. Biol. 1996; 41: 2009-20026).*
Milenic et al. (Nature Rev. Drug Discovery 3: 488-498, 2004).*
Dadachova et al. ("Radioimmunotherapy of Pigmented Melanoma with Melanin-Targeting Antibody," In Program of Ninth Conference on Cancer Therapy with Antibodies and Immunoconjugates, Oct. 22, 2002, Abstract, P-08).*
Kobayashi et al. (Cancer Research 1996; 56: 3788-3795).*
Allen BJ, Rizvi SM, Tian Z., entitled "Preclinical targeted alpha therapy for subcutaneous melanoma," Melanoma Res 11: 175-182, 2001.
Charlton DE., entitled "The survival of monolayers of cells growing in clusters irradiated by 211-AT appended to the cell surfaces," Radiat Res. 151: 750-753, 1999.
Chen, J, Giblin MF, Wang N, Jurisson SS, Quinn TP, entitled In vivo evaluation of 99mTc/188Re-labeled linear alpha-melanocyte stimulating hormone analogs for specific melanoma targeting. Nucl Med Biol. Aug. 1999; 26(6): 687-93.
Cheng Z, Chen J, Miao Y, Owen NK, Quinn TP, Jurisson SS, entitled "Modification of the structure of a metallopeptide: synthesis and biological evaluation of (111) In-labeled DOTA- conjugated rhenium-cyclized alpha-MSH analogues," J Med Chem. Jul. 4, 2002;45(14): 3048-56.
Hill, HZ, entitled "The function of melanin or six blind people examine an elephant," Bioessays 14: 49-56, 1992.
Kinnaert E, Morandini R, Simon S, Hill HZ, Ghanem G, Van Houtte P, entitled "The degree of pigmentation modulates the radiosensitivity of human melanoma cells," Radiat Res. 154: 497-502, 2000.
Kwok CS, Civici A, MacGregor WD, Unger MW, entitled "Optimization of radioimmunotherapy using human malignant melanoma mutlicell spheroids as a model," Cancer Res. 49: 3276-3281, 1989.
Lindmo T, Boven E, Mithcell JB, Morstyn G, Bunn PA Jr., entitled "Specific Killing of human melanoma cells by 125I- labeled 9.2.27 monoclonal antibody," Cancer Res. 45: 5080-5087, 1985.

(Continued)

*Primary Examiner*—Brandon J Fetterolf
(74) *Attorney, Agent, or Firm*—Amster, Rothstein & Ebenstein LLP

(57) ABSTRACT

This invention provides methods for imaging and/or treating a tumor in a subject which comprise administering to the subject an amount of a radiolabeled antibody effective to image and/or treat the tumor, where the radiolabeled antibody binds to a cellular component released by dying tumor cells. This invention also provides methods for imaging and/or treating melanin-containing melanomas in a subject which comprise administering to the subject an amount of a radiolabeled anti-melanin antibody effective to image and/or treat the melanoma. The invention also provides compositions and methods of making compositions comprising radiolabeled antibodies for imaging and treating tumors, including melanin-containing melanomas.

32 Claims, 11 Drawing Sheets

OTHER PUBLICATIONS

Ong GL, Elsamra SE, Goldenberg DM, Mattes MJ, entitled Single-cell cytotoxicity with radiolabeled antibodies. Clin Cancer Res 7: 192-201, 2001.

Rofstad, EK, entitled "Radiation biology of malignant melanoma," Acta Radiol. Oncol. 25 1-10, 1986.

Dadachova, E et al., entitled "Melanin-targting antibody as a potential agent for radioimmunotherapy of melanoma," World Journal of Nuclear Medicine, vol. 1, Supplement 2, Sep. 2002, S275, Abstract.

Dadachova, E et al., entitled "Radioimmunotherapy of Pigmented Melanoma with Melanin-Targeting Antibody," In Program of Ninth Conference on Cancer Therapy with Antibodies and Immunoconjugates, Oct. 2002, Abstract, P-08.

Rosas et al., "Passive immunization with melanin-binding monoclonal antibodies prolongs survival of mice with lethal cryptococcus neoformans infection." Infection and Immunity, 3410-3412, May 2001.

* cited by examiner

A

B

A

B

A

B

RADIOLABELED ANTIBODIES FOR TREATMENT OF TUMORS

PRIORITY CLAIM

This application claims the benefit of U.S. Provisional Application No. 60/446,684, filed Feb. 11, 2003, the content of which is hereby incorporated by reference in its entirety into the subject application.

STATEMENT OF GOVERNMENT SUPPORT

The invention disclosed herein was made with U.S. Government support under grant number KO8 AI-01489 from the National Institutes of Health, U.S. Department of Health and Human Services. Accordingly, the U.S. Government has certain rights in this invention.

FIELD OF THE INVENTION

The present invention relates to the imaging and treatment of melanin-containing melanomas using radiolabeled anti-melanin antibodies, and to the imaging and treatment of tumors using radiolabled antibodies that bind to a cellular component released by dying tumor cells.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

There is a clinical need for new therapies for melanoma which is among the few cancers with a rising incidence (1). Malignant melanoma affects ~40,000 new patients each year in the United States and an estimated 100,000 world-wide (2, 3). Melanoma is an important cause of cancer among young patients (30-50 years) which increases the economic importance of the disease. While primary tumors are successfully removed surgically, a satisfactory treatment for patients with metastatic melanoma has not been developed (4). The median survival time of patients with metastatic melanoma is 8.5 months, with an estimated 5-year survival of 6% (4). There has been little change in these results over the past 25 years.

Immune approaches to the therapy of metastatic melanoma have been evolving steadily and include treating patients with 1) non-specific immune stimulants with a focus on the use of tumor-associated antigens by passive immune therapy with antibodies targeted directly to tumor cells; and 2) active immune therapy via vaccination with tumor cells, tumor cell lysates, peptides, carbohydrates, gene constructs encoding proteins, or anti-idiotype antibodies that mimic tumor-associated antigens (5).

Monoclonal antibodies (mAbs) radiolabeled with diagnostic radioisotopes 99 m-Technetium ($^{99m}$Tc) and 111-Indium ($^{111}$In) as well as with $^{131}$-Iodine ($^{131}$I) have been used extensively for radioimmunoimaging (RII) of metastatic melanoma. A recent review by Kang and Yong (6) summarizes 58 patient trials (excluding case studies) involving a total of 3638 patients. The majority (>80%) of these studies used mAbs to high molecular weight melanoma associated antigen (HMW-MAA) proteoglycan. The sensitivity of RII using various anti-HMW-MAA mAbs or mAbs against other melanoma associated antigens such as P97 (7) is 65-88% (5, 6) which compares favorably with standard diagnostic methods (6). RII is also able to survey the entire body for metastases in a single study and can detect a substantial number of otherwise occult lesions.

Although RII has filled a niche in detection and disease assessment of metastatic melanoma, the ultimate goal is radioimmunotherapy (RIT). RIT takes advantage of the specificity of the antigen-antibody interaction to deliver lethal doses of radiation to target cells using radiolabeled antibodies (8). RIT is experiencing a renaissance, and so far has been most successful for the treatment of "liquid" and "semi-liquid" malignancies such as lymphoma and leukemia (9). The recent FDA approval of Zevalin® (IDEC Pharmaceuticals, San Diego, Calif.), which is 90-Yttrium ($^{90}$Y) labeled monoclonal anti-CD20 antibody for treatment of relapsed or refractory B-cell non-Hodgkin's lymphoma is proof of the enormous potential of RIT in cancer treatment.

There have been relatively few attempts to use RIT for treatment of melanoma in either the pre-clinical or clinical settings. One possible explanation for this might be the perception of melanoma as a relatively radioresistant cancer (10, 11) resulting from the outcomes of radiation therapy of melanoma with external beam radiation. Radioresistance in melanoma has been associated with melanin contents which presumably provide a non-specific shield that absorbs photons. The perception that melanoma is radioresistant is changing now (11) and, more importantly, it has been shown that radioresistance of certain tumors towards external radiation beam is higher compared to treatment of the same type of tumors with radioimmunotherapy. The difference in efficacy is due to different mechanisms of interaction between tumor cells and gamma rays of external beam compared to the particulate radiation delivered by radiolabeled antibodies (12, 13). Significant killing of melanoma cells in monolayers was observed as a result of treatment with antibodies radiolabeled with 125-Iodine (14), 211-Astatine (15), and 111-Indium (16). 131-I-labeled mAb caused shrinkage of human malignant melanoma multicellular spheroids (17). In an animal model of human melanoma, intratumoral injection of mAb radiolabeled with alpha-emitter 213-Bismuth caused complete disappearance of xenografted tumors while systemic RIT was less efficient with some delay in tumor progression followed by eventual re-growth (18). In a pilot study in patients with metastatic melanoma (19), a patient who received total dose of 374 mCi 131-I-labeled Fab' fragments of anti-HMW-MAA mAb showed a greater than 50% reduction in the size of pelvic and pericaval nodes, with stabilization of disease at the smaller nodal size for a period of several months.

The majority of human melanomas are pigmented with melanin. Although several antibodies have been tried for the therapy of melanomas (notably monoclonal antibodies against high molecular weight melanoma-associated antigen, against chondroitin sulfate proteoglycan, and against transferrin receptor), the approach of targeting melanin with an anti-melanin antibody has not been utilized. One factor which teaches away from the use of anti-melanin antibodies is that melanin is an intracellular pigment that is normally found in the melanosome. Hence, one might dismiss this pigment as a target as being inaccessible to a serum antibody. Another factor is that the amount of intracellular melanin is inversely related to the radiosensitivity of human melanoma cells (20-22). Melanin is thought to absorb radiation and thereby protect the cells.

SUMMARY OF THE INVENTION

The present invention is directed to the use of melanin as an antigen for radioimmunotherapy (RIT) of melanoma with radiolabeled anti-melanin antibodies. Targeting melanin with radiolabeled antibodies allows the use of RIT against melanomas that contain melanin, i.e. pigmented melanomas and hypomelanotic melanomas which are the most common types of melanoma. Accordingly, the invention provides a method for treating a melanin-containing melanoma in a subject which comprises administering to the subject an amount of a radiolabeled anti-melanin antibody effective to treat the melanoma. The invention also provides a method for imaging a melanin-containing melanoma in a subject which comprises administering to the subject an amount of a radiolabeled anti-melanin antibody effective to image the melanoma.

This invention further provides methods of treating and/or imaging a tumor in a subject which comprise administering to the subject an amount of a radiolabeled antibody effective to treat and/or image the tumor, where the radiolabeled antibody binds to a cellular component released by a dying tumor cell.

The invention also provides a method of making a composition effective to treat or image a melanin-containing melanoma in a subject which comprises admixing a radiolabeled anti-melanin antibody and a carrier. The invention further provides a composition comprising an amount of a radiolabeled anti-melanin antibody effective to treat and/or image a melanin-containing melanoma in a subject and a carrier.

DETAILED DESCRIPTION OF THE INVENTION

Figure 1A:
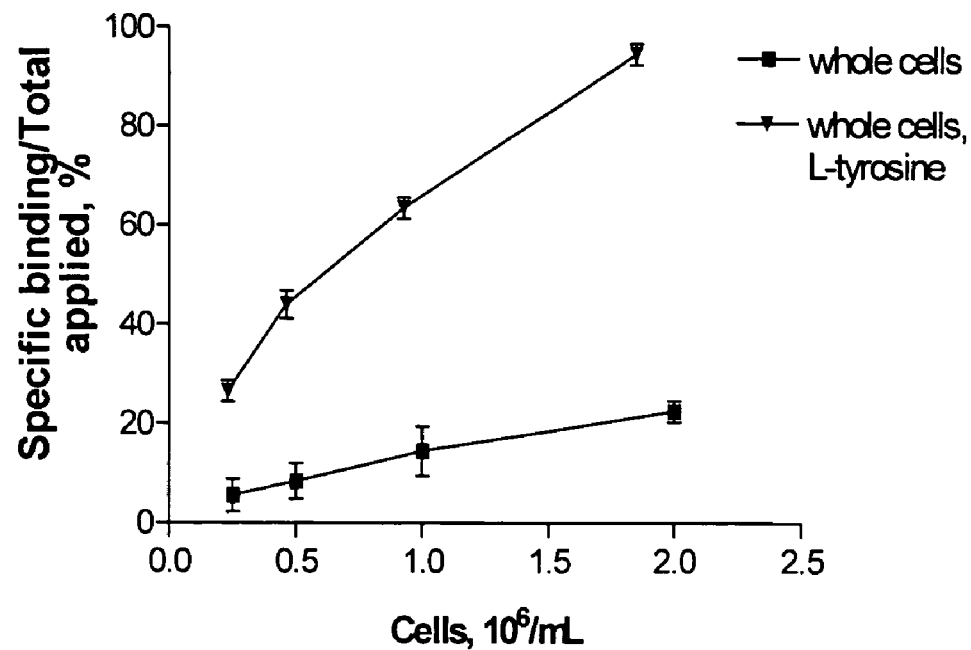
FIG. 1A-1B. Binding of $^{213}$Bi-CHXA"-6D2 to SK-MEL-28 cells (A) and to MNT1 cells (B).

This invention provides a method of treating a tumor in a subject which comprises administering to the subject an amount of a radiolabeled antibody effective to treat the tumor, where the radiolabeled antibody binds to a cellular component released by a dying tumor cell. The invention also provides a method of imaging a tumor in a subject which comprises administering to the subject an amount of a radiolabeled antibody effective to image the tumor, where the radiolabeled antibody binds to a cellular component released by a dying tumor cell. The cellular component can be a histone, a mitochondrial protein, a cytoplasmic protein, or a pigment, e.g. melanin. The histone can be one of the major subtypes of histones, i.e. H1, H2A, H2B, H3 and H4. In one embodiment, the tumor is a melanoma and the cellular component is melanin.

The subject invention is also directed to a method for treating a melanin-containing melanoma in a subject which comprises administering to the subject an amount of a radiolabeled anti-melanin antibody effective to treat the melanoma. The invention further provides a method for imaging a melanin-containing melanoma in a subject which comprises administering to the subject an amount of a radiolabeled anti-melanin antibody effective to image the melanoma.

As used in the subject application, the term "antibody" encompasses whole antibodies and fragments of whole antibodies. The application is also directed to uses of radiolabeled peptides in place of radiolabeled antibodies. Preferably, the peptide is positively charged. Antibody fragments include, but are not limited to, F(ab')$_2$ and Fab' fragments. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. The term antibody is further meant to encompass polyclonal antibodies and monoclonal antibodies. In one embodiment, the antibody fragment or peptide specifically binds to a cellular component released by a dying tumor cell. In one embodiment, the antibody fragment or peptide specifically binds to melanin.

The antibody can be any of an IgA, IgD, IgE, IgG, or IgM antibody. The IgA antibody can be an IgA1 or an IgA2 antibody. The IgG antibody can be an IgG1, IgG2, IgG2a, IgG2b, IgG3 or IgG4 antibody. A combination of any of these antibodies can also be used. One consideration in selecting the type of antibody to be used is the desired serum half-life of the antibody. IgG has a serum half-life of 23 days, IgA 6 days, IgM 5 days, IgD 3 days, and IgE 2 days (60). Another consideration is the size of the antibody. For example, the size of IgG is smaller than that of IgM allowing for greater penetration of IgG into tumors. IgA, IgG, and IgM are preferred antibodies.

In one embodiment, the antibody is 6D2. In one embodiment, the antibody is an antibody generated against human melanin.

Melanin-binding peptides have been described (24), where the melanin-binding peptide is a decapeptide. In one embodiment, the melanin-binding decapeptide is 4B4 (YERKFWH-GRH) (SEQ ID NO:1) (24). Melanin-binding peptides longer or shorter than 10 amino acids can also be used. Important structural characteristic of melanin-binding peptides are the presence of aromatic amino acids and overall positive charge.

As used herein, the term "tumor" includes melanomas. The term "treat" a tumor means to eradicate the tumor, to reduce the size of the tumor, to stabilize the tumor so that it does not increase in size, or to reduce the further growth of the tumor.

The subject can be a mammal. In different embodiments, the mammal is a mouse, a rat, a cat, a dog, a horse, a sheep, a cow, a steer, a bull, livestock, a primate, a monkey, or preferably a human.

The choice of the particular radioisotope with which the antibody is labeled may be determined by the size of the tumor to be treated and its localization in the body. Two characteristics are important in the choice of a radioisotope—emission range in the tissue and half-life. Alpha emitters, which have a short emission range in comparison to beta emitters, may be preferable for treatment of small tumors or melanomas that are disseminated in the body. Examples of alpha emitters include 213-Bismuth (half-life 46 minutes), 223-Radium (half-life 11.3 days), 224-Radium (half-life 3.7 days), 225-Radium (half-life 14.8 days), 225-Actinium (half-life 10 days), 212-Lead (half-life 10.6 hours), 212-Bismuth (half-life 60 minutes), 211-Astatin (half-life 7.2 hours), and 255-Fermium (half-life 20 hours). In a preferred embodiment, the alpha-emitting radioisotope is 213-Bismuth). $^{213}$Bi emits a high LET α-particle with E=5.9 MeV with a path length in tissue of 50-80 μm. Theoretically a cell can be killed with one or two α-particle hits. $^{213}$Bi has been proposed for use in single-cell disorders and some solid cancers (34, 35-37) and has been used to treat patients with leukemia in Phase I clinical trials (38, 39). $^{213}$Bi is the only α-emitter that is currently available in generator form, which allows transportation of this isotope from the source to clinical centers within the United States and abroad.

Beta emitters, with their longer emission range, may be preferable for the treatment of large tumors or melanomas. Examples of beta emitters include 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131-Iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199-Gold (half-life 3.1 days). In a preferred embodiment, the beta-emitting radioisotope is 188-Rhenium. $^{188}$Re is a high-energy β-emitter ($E_{max}$=2.12 MeV) that has recently emerged as an attractive therapeutic radionuclide in diverse therapeutic trials including cancer radioimmunotherapy, palliation of skeletal bone pain, and endovascular brachytherapy to prevent restenosis after angioplasty (31-33). $^{118}$Re has the additional advantage that it emits γ-rays which can be used for imaging studies. For the treatment of large tumors or melanomas or those in difficult to access sites deep in the body, longer-lived isotopes such as 90-Yttrium (half-life 2.7 days), 177-Lutetium (half-life 6.7 days) or 131-Iodine (half-life 8 days) may be preferred.

Positron emitters could also be used, such as (half-life in parenthesis): $^{52m}$Mn (21.1 min); $^{62}$Cu (9.74 min); $^{68}$Ga (68.1 min); $^{11}$C (20 min); $^{82}$Rb (1.27 min); $^{110}$In (1.15 h); $^{118}$Sb (3.5 min); $^{122}$I (3.63 min); $^{18}$F (1.83 h); $^{34m}$Cl (32.2 min); $^{38}$K (7.64 min); $^{51}$Mn (46.2 min); $^{52}$Mn (5.59 days); $^{52}$Fe (8.28 h); $^{55}$Co (17.5 h); $^{61}$Cu (3.41 h); $^{64}$Cu (12.7 h); $^{72}$As (1.08 days); $^{75}$Br (1.62 h); $^{76}$Br (16.2 h); $^{82m}$Rb (6.47 h); $^{83}$Sr (1.35 days); $^{86}$Y (14.7 h); $^{89}$Zr (3.27 days); $^{94m}$Tc (52.0 min); $^{120}$I(1.35h); $^{124}$I (4.18 days). 64-Copper is a mixed positron, electron and Auger electron emitter.

Any of the radioisotopes, except alpha emitters, that are used for radioimmunotherapy can also be used at lower doses for radioimmunoimaging, for example a beta emitter, a positron emitter or an admixture of a beta emitter and a positron emitter. Preferred radioisotopes for use in radioimmunoimaging include 99 m-Technetium, 111-Indium, 67-Gallium, 123-Iodine, 124-Iodine, 131-Iodine and 18-Fluorine. For imaging one can use a dose range of 1-30 mCi for diagnostic isotopes (e.g., 99 m-Tc) and 1-5 mCi for therapeutic isotopes to avoid unnecessary dose to a patient.

The invention further provides methods for treating tumors or melanin-containing melanoma in a subject which comprise administering to the subject an amount of antibodies radiolabeled with a plurality of different radioisotopes effective to treat the tumor. Preferably, the radioisotopes are isotopes of a plurality of different elements. In a preferred embodiment, at least one radioisotope in the plurality of different radioisotopes is a long range emitter and at least one radioisotope is a short range emitter. Examples of long range emitters include beta emitters and positron emitters. Examples of short range emitters include alpha emitters. Positron emitters can also be intermediate range emitters depending on the energy of the positrons. In a preferred embodiment, the long-range emitter is a beta emitter and the short range emitter is an alpha emitter. Preferably, the beta emitter is 188-Rhenium. Preferably, the alpha emitter is 213-Bismuth. Combinations of different radioisotopes can be used, which include an admixture of any of an alpha emitter, a beta emitter, and a positron emitter, with physical half-lives from 30 minutes to 100 days. Preferably, the plurality of different radioisotopes is more effective in treating the tumor than a single radioisotope within the plurality of different radioisotopes, where the radiation dose of the single radioisotope is the same as the combined radiation dose of the plurality of different radioisotopes.

It is known from radioimmunotherapy studies of tumors that whole antibodies usually require from 1 to 3 days time in circulation to achieve maximum targeting. While slow targeting may not impose a problem for radioisotopes with relatively long half-lives such as $^{188}$Re ($t_{1/2}$=16.7 hours), faster delivery vehicles are needed for short-lived radioisotopes such as $^{213}$Bi ($t_{1/2}$=46 min). The smaller melanin-binding peptides and F(ab')$_2$ and Fab' fragments provide much faster targeting which matches the half-lives of short-lived radionuclides (55, 56).

The dose of the radioisotope can vary depending on the localization and size of the tumor, the method of administration of radiolabeled antibody (local or systemic) and the decay scheme of the radioisotope. In order to calculate the doses which can treat the tumor without radiotoxicity to vital organs, a diagnostic scan of the patient with the antibody radiolabeled with a diagnostic radioisotope or with a low activity therapeutic radioisotope can be performed prior to therapy, as is customary in nuclear medicine. The dosimetry calculations can be performed using the data from the diagnostic scan (59). In different embodiments, the dose of the radioisotope for RIT is between 1-1000 mCi.

Clinical data (39, 58) indicate that fractionated doses of radiolabeled antibodies and peptides are more effective than single doses against tumors and are less radiotoxic to normal organs. Depending on the status of a patient and the effectiveness of the first treatment with RIT, the treatment may consist of one dose or several subsequent fractionated doses.

The uptake of radiolabeled antibody by the kidney can be reduced or inhibited by administering a positively charged amino acid to the subject (29, 30), such as lysine, arginine or histidine. A preferred amino acid is D-lysine.

Preferably, the uptake of radiolabeled anti-melanin antibody in the melanoma or radiolabled antibody in the tumor is at least 10 times greater than in surrounding muscle. Preferably, the radiolabeled anti-melanin antibody is not taken up by non-cancerous (i.e., normal or healthy) melanin-containing tissue, including, but not limited to, hair, eyes, skin, brain, spinal cord, and/or peripheral neurons.

The invention provides a method of using a radiolabeled anti-melanin antibody to image and/or treat a melanin-containing melanoma in a subject which comprises:

(a) generating a monoclonal antibody against melanin;

(b) attaching a radiolabel to the monoclonal antibody; and (c) administering to the subject an amount of the radiolabeled antibody effective to image and/or treat the melanoma.

The invention further provides a method of using a radiolabeled antibody to image and/or treat a tumor in a subject which comprises:

(a) generating a monoclonal antibody against a cellular component released by a dying tumor cell;

(b) attaching a radiolabel to the monoclonal antibody; and (c) administering to the subject an amount of the radiolabeled antibody effective to image and/or treat the tumor.

Antibodies can be readily generated without undue experimentation using the protocol given below in Experimental Details.

The invention provides a method of making a composition effective to treat a melanin-containing melanoma in a subject which comprises admixing a radiolabeled anti-melanin antibody and a carrier. The invention also provides a method of making a composition effective to image a melanin-containing melanoma in a subject which comprises admixing a radiolabeled anti-melanin antibody and a carrier. The invention further provides a method of making a composition effective to image and/or treat a tumor in a subject which comprises admixing a radiolabeled antibody and a carrier, where the antibody binds to a cellular component released by a dying tumor cell. The invention provides a composition made by any of these methods, i.e. a composition comprising an anti-melanin antibody effective to treat and/or image a melanin-containing melanoma in a subject and a carrier. As used herein, the term "carrier" encompasses any of the standard pharmaceutical carriers, such as a sterile isotonic saline, phosphate buffered saline solution, water, and emulsions, such as an oil/water emulsion.

In different embodiments, a melanin-containing melanoma can be a pigmented melanoma, a hypomelanotic melanoma, or an amelanotic melanoma. So-called "amelanotic melanomas" are generally hypomelanotic and contain small amounts of melanin (61, 62).

This invention will be better understood from the Experimental Details which follow. However, one skilled in the art will readily appreciate that the specific methods and results discussed are merely illustrative of the invention as described more fully in the claims which follow thereafter.

Experimental Details

1. Introduction

Melanin is an intracellular pigment that is normally found in the melanosome. Hence, one might dismiss this pigment as a target for a serum antibody because melanin could be expected to be inaccessible. However, melanomas, like many rapidly growing tumors, can be assumed to have a large cell turnover resulting in cell lysis and release of pigment. Hence, an antibody to melanin can bind to melanin by virtue of the presence of extracellular pigment originating from dead cells. Furthermore, since most of the melanin in the body in healthy tissue is intracellular, it is believed that antibody therapy targeting melanin would not harm pigmented cells such as normal melanocytes or melanin-containing neurons.

Monoclonal antibodies have been developed against fungal melanin produced by *C. neoformans*. These mAbs bind to melanin produced by other microorganisms such as *Sepia officinalis* as well as to synthetic melanin (23-25). Since both fungal melanin and melanin in tumors are negatively charged and reagents generated to fungal melanin recognize melanin from diverse sources (25, 26), it was hypothesized that fungal melanin-binding antibody would bind to melanin in melanoma cells and would be able to deliver radioisotopes to the tumors in vivo.

2. Materials and Methods

Radiolabeled anti-melanin antibodies. An anti-melanin antibody (mAb 6D2) that was originally developed against fungal melanin (23) was used as a carrier delivery vehicle to deliver therapeutic radioactivity (e.g. radioimmunotherapy (RIT)) to a pigmented melanoma. MAb 6D2 (IgM type) was generated from hybridomas obtained from mice immunized with melanin isolated from *Cryptococcus neoformans*. $Na^{99m}TcO_4$ was purchased from Syncor (Bronx, N.Y.), and $^{111}InCl_3$ from Iso-Tex Diagnostics, Friendswood, Tex. $^{188}Re$ in the form of Na perrhenate ($Na^{188}ReO_4$) was eluted from a $^{188}W/^{188}Re$ generator (Oak Ridge National Laboratory (ORNL), Oak Ridge, Tenn.). 225-Actiunium ($^{225}Ac$) for construction of a $^{225}Ac/^{213}Bi$ generator was acquired from ORNL. The $^{225}AC/^{213}Bi$ generator was constructed using a MP-50 cation exchange resin, and $^{213}Bi$ was eluted with 0.15 M HI (hydroiodic acid) in the form of $^{213}BiI_3$ as described in (52). The mAb was radiolabeled with $^{213}Bi$ (213-Bismuth, short-range alpha-emitting isotope for therapy) or $^{111}In$ (111-Indium, photon emitter for imaging use, chemical analogue of $^{213}Bi$) via the bifunctional chelator CHXA" (N-[2-amino-3-(p-isothiocyanatophenyl)propyl]-trans-cyclohexane-1,2-diamine-N, N', N", N''', N''''-pentaacetic acid) (57); and with $^{188}Re$ (188-Rhenium, long-range beta-emitting isotope for therapy) and $^{99m}Tc$ (99 m-Technetium, photon emitter for imaging, chemical analogue of $^{188}Re$) via "direct labeling" through reduction of antibody disulfide bonds with dithiothreitol (54). The immunoreactivity of radiolabeled 6D2 mAb towards fungal melanin was tested by immunofluorescence.

Radiolabeled melanin-binding peptides. Fungal melanin-binding peptides have been previously identified and sequenced from the phage display library (24). The melanin-binding decapeptide 4B4 (YERKFWHGRH) (SEQ ID NO:1) was synthesized with HYNIC (hydrazinonicotinamide) ligand at the N terminus utilizing D-amino acids and Fmoc reagent 6-Fmoc-hydrazino-nicotinic acid (Trilink Biotechnology, Inc.) in the Laboratory for Macromolecular Analysis at Albert Einstein College of Medicine, Bronx, N.Y. The peptide structure was verified by mass spectrometry and amino acid sequencing. HYNIC-D-4B4 was radiolabeled with $^{188}Re$.

In vivo studies. Studies were carried out by injecting human melanoma cells into nude mice. The use of nude mice is essential to prevent the mouse immune system from clearing the human cells. In one set of experiments, the human lightly pigmented melanoma line SK-28-MEL (ATCC) was used. Mice were injected IP with $2.8 \times 10^6$ SK-28-MEL cells 24 hours before injections of radiolabeled antibody. In another set of experiments, melanoma-like lesions were created in nude mice using highly pigmented human melanoma cells MNT1 (27). Tumors were induced by injecting $5.5 \times 10^6$ MNT1 cells into the right flank of female nude mice. The tumors reached 0.7-1 cm in diameter 4 weeks after implantation.

3. Results

Figure 1B:
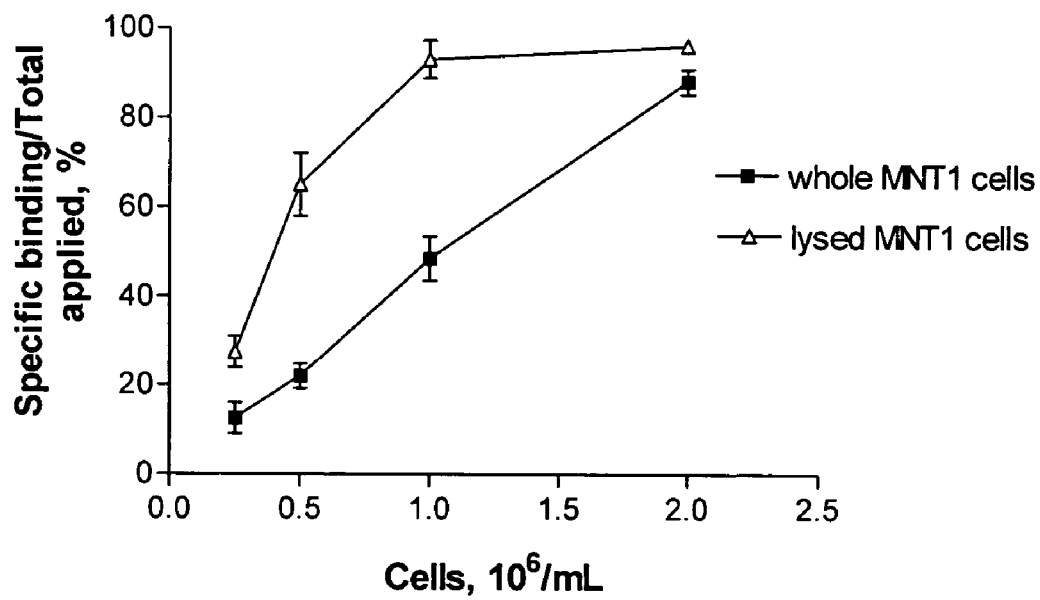

Binding of radiolabeled antibody to human pigmented melanoma cell line. Cell binding of $^{111}$In-6D2 and the irrelevant IgM 12A1 (which binds to *C. neoformans* capsule) was evaluated by incubating 2 µg/mL mAb with $0.23-2 \times 10^6$ whole cells of the human lightly pigmented melanoma line SK-28-MEL (ATCC) which was grown with or without 110 µM L-tyrosine to promote melanin formation. Cell binding of $^{111}$In-6D2 (FIG. 1A) was higher for the melanoma cells grown with 110 µM L-tyrosine suggesting melanin-specific binding. The binding of $^{111}$In-6D2 antibody to SK-MEL-28 cells was due to the presence of extracellular melanin in the milieu which is constantly being released as a result of cell turn-over. For MNT1 cells significantly higher binding was observed for lysed cells which is almost certainly due to the release of melanin from the cells and making it accessible to the antibody (FIG. 1B).

Figures 2A, 2B, 2C:
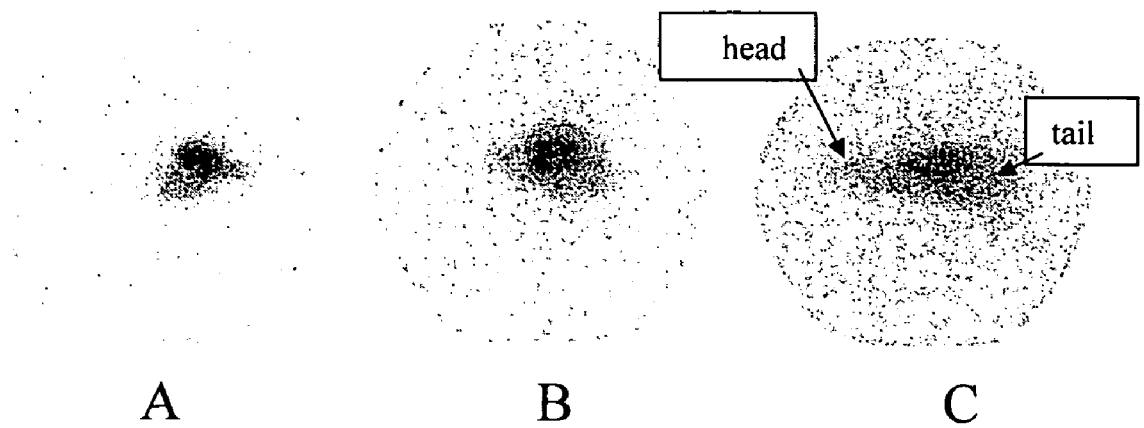
FIG. 2A-2C. Scintigraphic images of nude mice at 3 hours post-injection with: A) $^{111}$In-6D2, administered IP to mice following IP injection of $2.8 \times 10^6$ SK-28-MEL cells 24 hours earlier; B) $^{111}$In-IgM, administered IP to mice following IP injection of $2.8 \times 10^6$ SK-28-MEL cells 24 hours earlier; C) $^{111}$In-6D2, administered IP to non-tumor-bearing mice.

In vivo binding of radiolabeled antibody to SK-28-MEL melanoma cells. In vivo binding of $^{111}$In-6D2 and control $^{111}$In-IgM was studied by scintigraphic imaging in nude mice injected IP with $2.8 \times 10^6$ SK-28-MEL cells 24 hours before $^{111}$In-6D2 (FIG. 2A-2C). For comparison several non-tumor bearing mice were injected IP with $^{111}$In-6D2 mAb. In mice injected IP with SK-28-MEL cells there was more retention of $^{111}$In-6D2 in the intraperitoneal cavity (FIG. 2A) compared to irrelevant $^{111}$In-IgM (FIG. 2B) and control animals with no tumor cells (FIG. 2C).

Figures 3A, 3B:
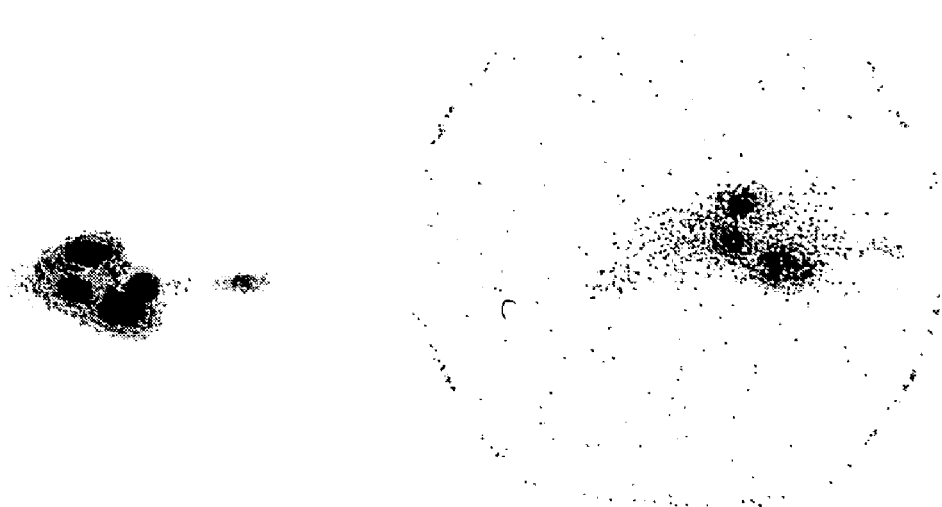
FIG. 3A-3B. Scintigraphic images of MNT1 tumor-bearing nude mouse at 3 hours (A) and 24 hours (B) post-injection with $^{99m}$Tc-6D2 antibody.

Radioimmunotherapy of melanomas using radiolabeled antibody to melanin. Melanoma-like lesions were created in nude mice using highly pigmented human melanoma cells MNT1 (27). Tumors were induced by injecting $5.5 \times 10^6$ MNT1 cells into the right flank of female nude mice. The tumors reached 0.7-1 cm in diameter 4 weeks after implantation. Several tumor-bearing and control (no tumors) mice were imaged with 0.4 mCi $^{99m}$Tc-6D2 (IV injection). Excellent localization in the tumor was achieved at 3 hours (FIG. 3A) and remained high at 24 hours (FIG. 3B). Significant uptake of $^{99m}$Tc-6D2 antibody was also observed in kidneys which is, most likely, due to the fact that the complimentarity determining region (CDR) of the antibody carries a positive charge which attracts antibody molecules to the negatively charged sites in the membranes of renal tubular cells (28). Alternatively, damaged radiolabeled antibody molecules may be cleared by the kidney. Blocking the kidneys with positively charged amino acids, such as D-lysine (29, 30), or using better defined preparations of labeled IgM may help in circumventing uptake of antibody by the kidney.

Binding of anti-melanin mAb 6D2 to MNT1 melanoma cells in vitro. To prove that mAb 6D2, which had been developed against fungal melanin, could also bind to tumor-derived melanin and to elucidate the mechanism of mAb 6D2 binding to MNT1 melanoma cells in vitro, the binding of this mAb to MNT1 cells was studied by immunofluorescence. The mAb 6D2 bound only to dead melanoma cells which comprised 3-5% of the total number of cells in culture as measured by the dye exclusion assay. Dead cells apparently released their melanin or had disrupted cell membranes that allowed antibody access to melanin. No binding was observed to viable cells with intact cell membranes. Control mAb 5C11 did not bind to either viable or dead MNT1 cells (results not shown).

Figure 4:
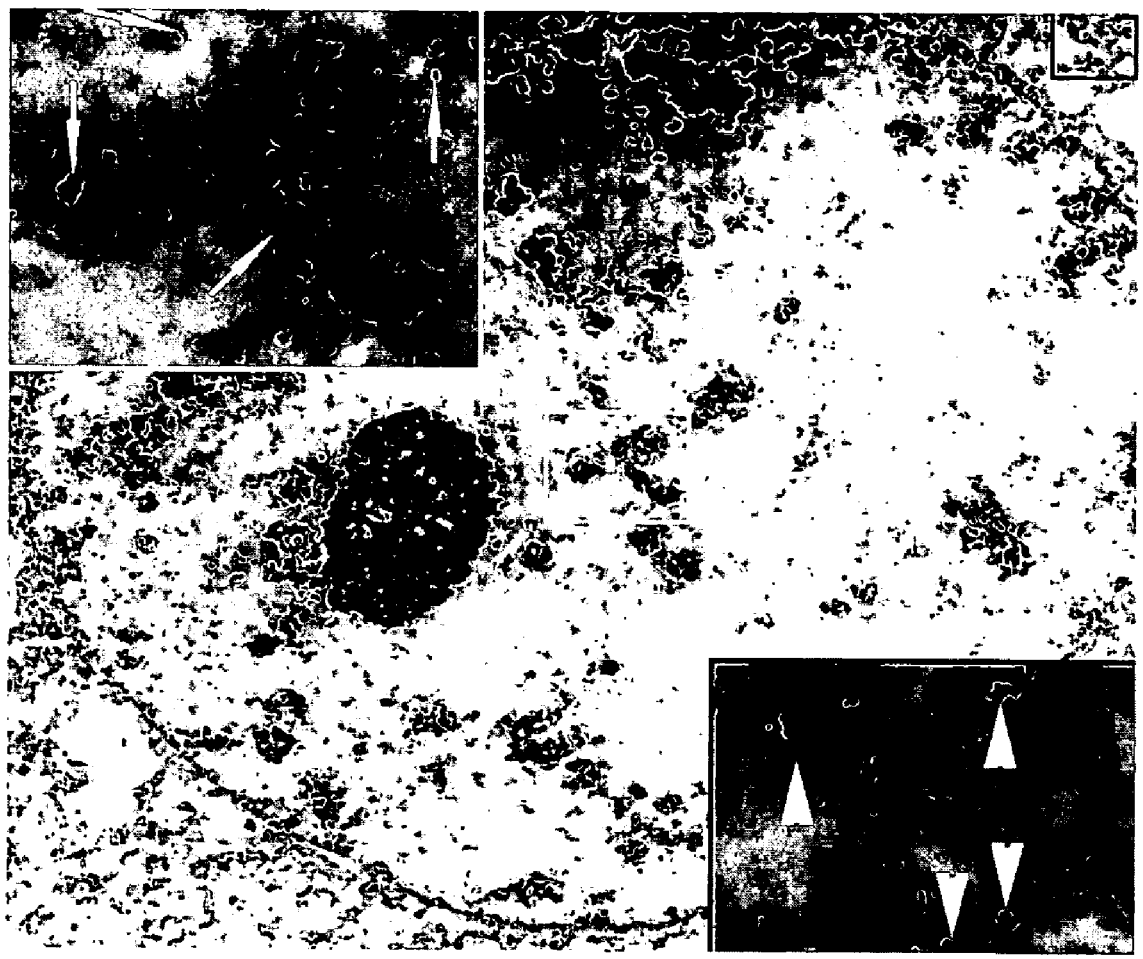
FIG. 4. Immunogold TEM of MNT1 melanoma cell stained with mAb 6D2 [original magnification×20,000]. Left upper corner inset is the magnification of the central area of the melanoma cell indicated by the white box near the center of the image; right lower corner inset is the magnification of the extracellular area indicated by the black box in the upper right corner of the image. Arrows indicate gold balls labeling melanin.

Binding of anti-melanin mAb 6D2 to tumor melanin. Immunogold transmission electron microscopy TEM experiments were performed to establish at the ultrastructural level whether mAb 6D2 could interact with tumor melanin. TEM of the tumor tissue arising from the human melanoma cell line MNT1 implanted into nude mice proved that mAb 6D2 bound to tumor melanin synthesized in vivo. Gold balls were associated with melanin particles inside the cell (FIG. 4, upper insert). By this method cytoplasmic melanin is made accessible to the antibody when the tissue is sectioned. However, the presence of extracellular melanin was almost certainly the result of melanin release from melanoma cells undergoing rapid cell turnover in a fast growing tumor (FIG. 4, lower inset). No association of gold balls with melanin was observed when the tumor tissue was stained with an irrelevant IgM (not shown).

Figure 5:
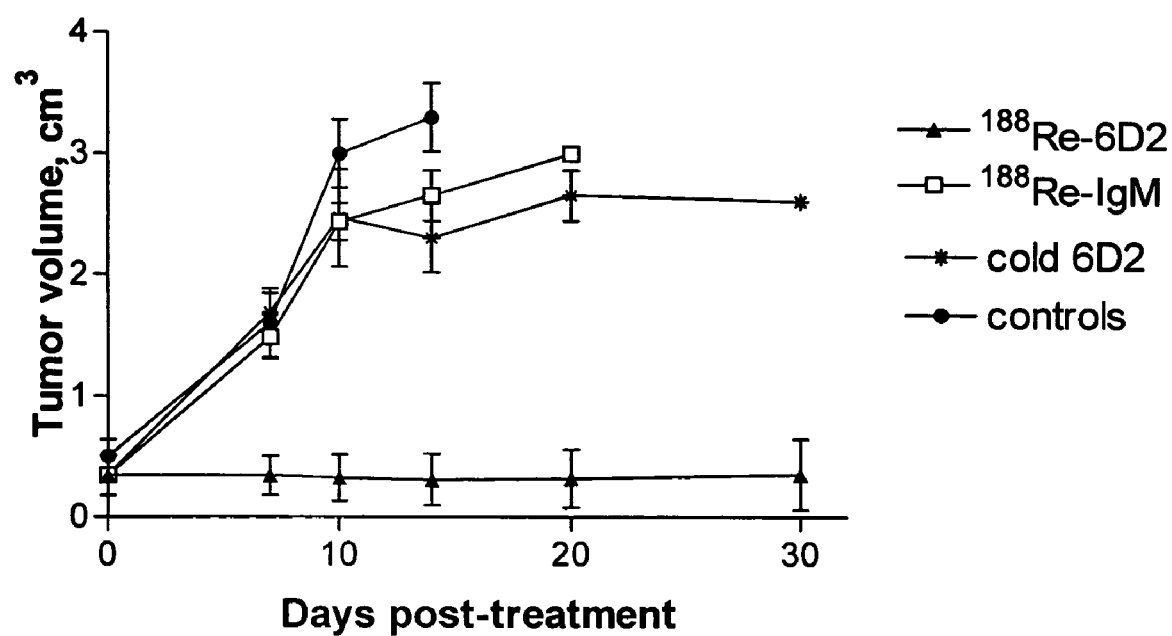
FIG. 5. MNT1 human melanoma tumor growth in nude mice treated with: 1.5 mCi $^{188}$Re-6D2; 1.5 mCi $^{188}$Re-IgM; and 100 µg unlabeled 6D2.

Therapy of MNT1 melanoma in nude mice with $^{188}$Re-6D2. For therapy experiments MNT1 tumor-bearing mice were separated into 4 groups of 7-8 animals and treated IV with: 1.5 mCi $^{188}$Re-6D2; 1.5 mCi $^{188}$Re-IgM; 100 µg unlabeled 6D2 or left untreated. Growth was completely inhibited in the group treated with $^{188}$Re-6D2 (FIG. 5), and tumor regression occurred in animals with smaller initial tumors. Residual thin (~1 mm) melanin plaques remained in mice with regressed tumors until they were sacrificed at day 30 after treatment. During the observation period, no deaths occurred in the mice treated with $^{188}$Re-6D2. In contrast, tumors continued to grow aggressively in mice treated with $^{188}$Re-IgM or unlabeled 6D2 and in the untreated mice. By day 20 post-treatment all control mice, except for one in the unlabeled 6D2 group, had died.

Biodistribution of radiolabeled melanin-binding peptide. Nude mice bearing MNT1 melanoma tumors were injected IV with 2 µg $^{188}$Re-HYNIC-D-4B4. Animals (groups of 4 per time point) were sacrificed at 30 min, 1, 2, 3 and 24 hours post-injection, and their major organs were removed, blotted from blood, weighted and counted in a gamma camera. To investigate if co-injection of D-lysine changes kidney and tumor uptake of $^{188}$Re-HYNIC-D-4B4, the peptide was co-injected IV with D-lysine (400 mg/kg) and the biodistribution was performed as above.

Figure 6A:
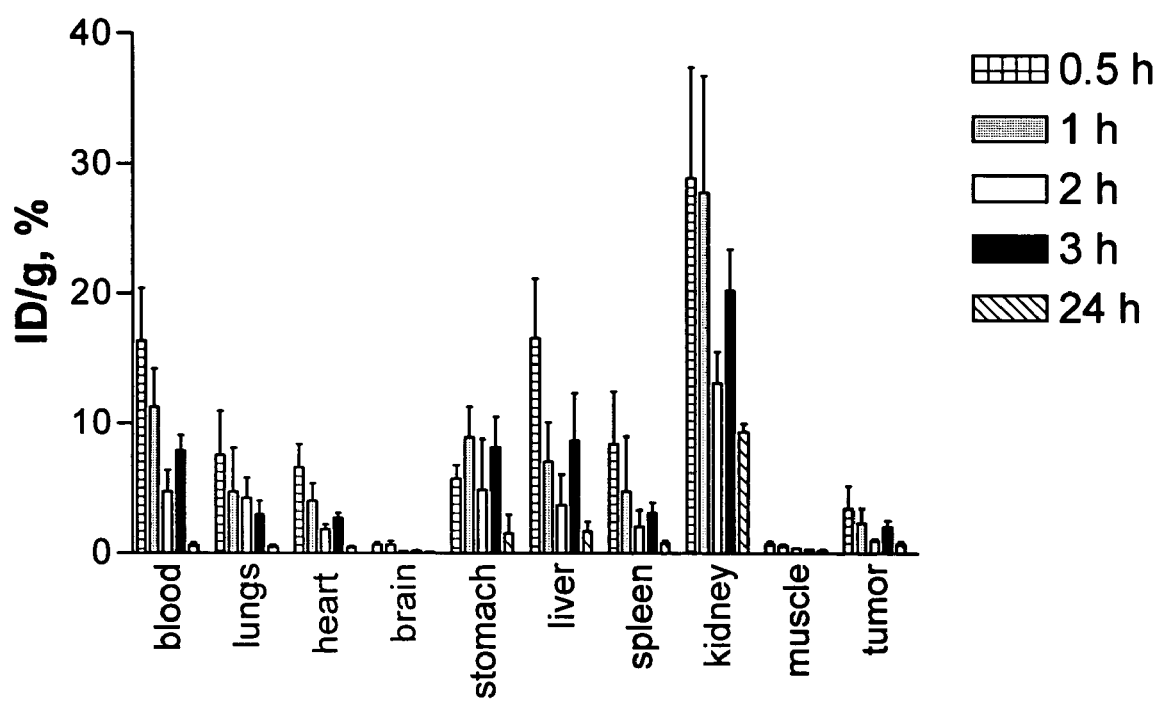
FIG. 6A-6B. Biodistribution of $^{188}$Re-HYNIC-D-4B4 in nude mice carrying MNT1 tumors. A) mice treated with only $^{188}$Re-HYNIC-D-4B4; B) mice treated with $^{188}$Re-HYNIC-D-4B4 plus D-lysine.

$^{188}$Re-HYNIC-D-4B4 cleared rapidly from the blood with only 0.5% ID/g remaining in circulation at 24 hours post-injection (FIG. 6A). Interestingly, a transient increase in uptake in practically all major organs was observed at 3 hours post-injection, which might be explained by the redistribution of activity from the intestinal compartment. The kidney uptake was high with ~30% ID/g being found in the kidneys at 0.5-1 hour post-injection, which decreased to 10% ID/g at 24 hours, which closely resembles the biodistribution pattern of $^{188}$Re-6D2 mAb. The tumor uptake of $^{188}$Re-HYNIC-D-4B4 was the highest at earlier time points (~4.5% ID/g) and decreased to 0.5% ID/g at 24 hours. At all times uptake of $^{188}$Re-HYNIC-D-4B4 in the tumor was 10 times higher than in surrounding muscle tissue.

Figure 6B:
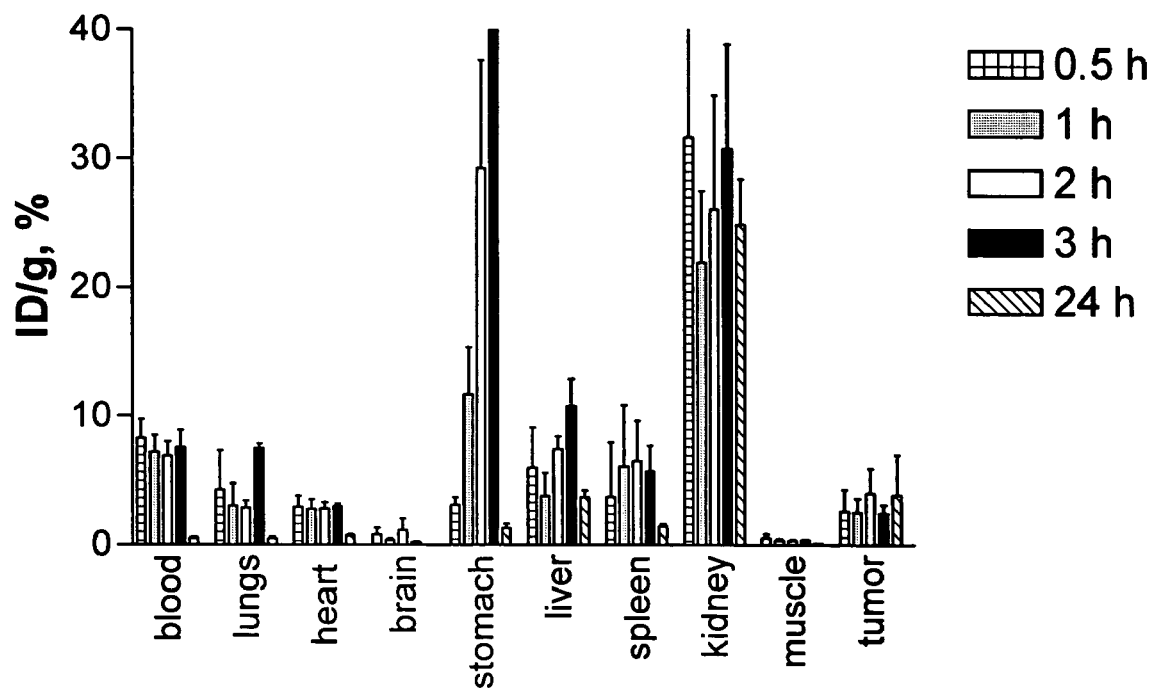

The biodistribution pattern changed somewhat when $^{188}$Re-HYNIC-D-4B4 was co-injected with D-lysine (FIG. 6B). Less uptake was observed in the blood, liver, spleen and heart. The redistribution of activity at 3 hours resulted in significantly elevated uptake in the stomach which resolved by 24 hours. Co-injection of D-lysine did not significantly change kidney uptake of $^{188}$Re-HYNIC-D-4B4 at 0.5-3 hour time points and increased it at 24 hours. The plausible explanation could be that $^{188}$Re-HYNIC-D-4B4 carries a much higher positive charge than D-lysine and, as a consequence, has higher affinity for the negatively charged sites on the membranes of renal tubular cells. The tumor uptake at 0.5 hour was the same as when no D-lysine was co-injected, but no wash-out of activity from the tumor was observed at later time points. It should be pointed out that the actual necessity of blocking kidney uptake in patients treated with radiolabeled peptides arises only when the cumulative dose to the kidney is likely to exceed 30 Gy (63).

Figure 7:
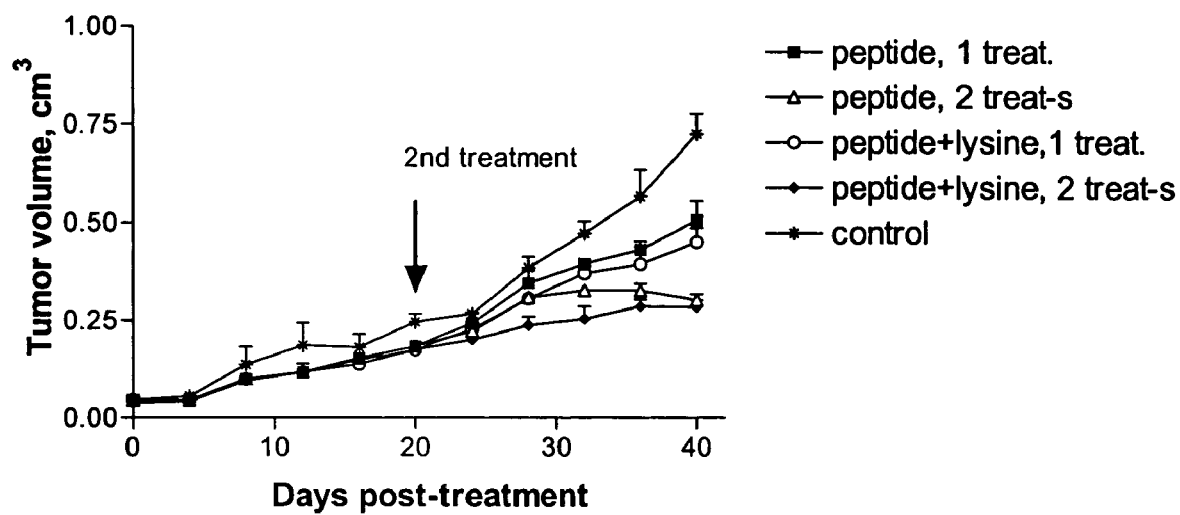
FIG. 7. Therapy of MNT1 melanoma tumors in nude mice with $^{188}$Re-HYNIC-D-4B4.

Radioimmunotherapy of melanomas using radiolabeled melanin-binding peptide. For therapy experiments nude mice bearing MNT1 tumors 0.4-0.5 cm in diameter (10 animals per group) were injected IP with 1 mCi $^{188}$Re-HYNIC-D-4B4 (20 µg), 1 mCi $^{188}$Re-HYNIC-D-4B4+10 mg (400 mg/kg body weight) D-lysine, or left untreated. On Day 20 post-treatment, 5 mice out of each treatment group were treated again with 1 mCi peptide or 1 mCi peptide +D-lysine to investigate the effect of multiple treatments on tumor progression. The size of the tumor was measured with calipers every 4 days. The tumors grew in the control group, and at somewhat slower pace in groups that received one treatment, and significantly slower (P=0.01) in groups that were treated twice (FIG. 7). It might be possible that multiple treatments with lower activities of radiolabeled peptides will be even more efficient in arresting melanoma tumors growth.

Safety of RIT of melanoma with melanin-binding antibodies. Comparative scintigraphic imaging of black and white mice with $^{188}$Re-6D2 mAb. In order to determine if $^{188}$Re-6D2 mAb binds to normal melanocytes, comparative imaging was performed using C57BL/6 black mice and BALB/c white mice. C57BL/6 mice have black hair, black eyes and melanized skin on their tails. Six C57BL/6 and six white BALB/c mice were injected IV with the same activity used in therapy experiments-1.5 mCi $^{188}$Re-6D2. Mice were imaged on a gamma camera 3 and 24 hours post-injection.

Figure 8A:
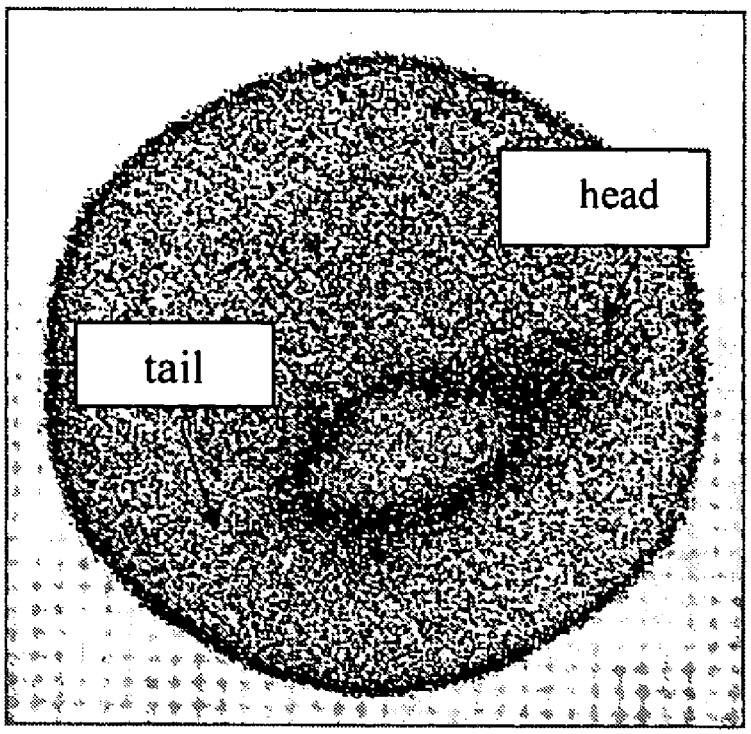
FIG. 8A-8B. Scintigraphic images of radiolabeled 6D2 mAb in black and white mice: A) 3 h image of $^{188}$Re-6D2 given IV to a black C57BL/6 mouse; B) 3 h image of $^{188}$Re-6D2 given IV to a white BALB/c mouse. The positions of the tails are marked with arrows.
Figure 8B:
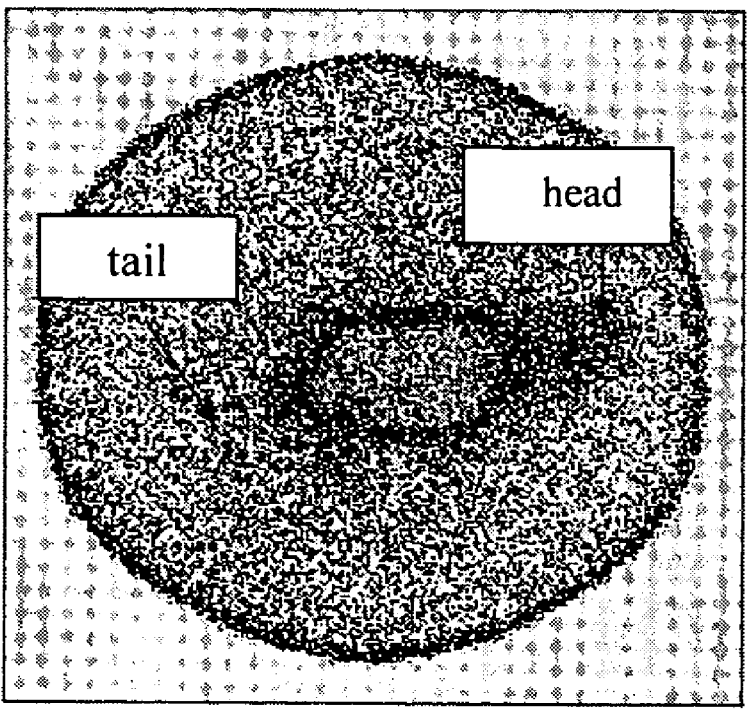
Figure 9A:
FIG. 9A-9B. Histological analysis of melanin-containing tissues of black C57BL/6 mice treated with $^{188}$Re-6D2 antibody: A—eye of a mouse treated with 1.5 mCi $^{188}$Re-6D2; B—eye of a control mouse.
Figure 9B:

No uptake of $^{188}$Re-6D2 was detected in the hair follicles, eyes, brains and melanized tails of C57BL/6 black mice at 3 hours (FIG. 8A) and at 24 hours (not shown) post-injection in comparison with white BALB/c mice (FIG. 8B). In order to determine if any radiation damage was induced by $^{188}$Re-6D2 mAb in melanin-containing normal tissues, three C57BL/6 black mice imaged with 1.5 mCi $^{188}$Re-6D2 and three control C57BL/6 mice were sacrificed 2 weeks post-imaging, followed by three other imaged and three other control mice at 4 weeks post-imaging. Their eyes and melanized skin from the tails were removed, formalin-fixed, paraffin-embedded, stained with hematoxylin and eosin, and analysed histologically. No radiation damage was detected in the eyes (FIG. 9) and melanized skin (results not shown) of C57BL/6 black mice treated with $^{188}$Re-6D2 mAb.

4. Prospective Examples

Generation of antibodies to cellular components that become accessible as a result of cell death. In addition to using anti-melanin antibodies, one can generate antibodies against proteins and other cellular components, such as histones, mitochondrial proteins, and cytoplasmic proteins, which are expressed only intracellularly in high concentrations and are released by dying cells, using well established hybridoma technology described below.

Generation of antibodies to human melanin. In addition to using the anti-melanin antibody illustrated herein, new mAbs to human melanin can be generated using for example melanin from melanoma cells as described below. Melanoma melanin can be purified as described in (40). Briefly, MNT1 highly pigmented human melanoma cells can be grown in MEM/20% FBS medium as in (27), collected and treated with the sequence of cell wall-lysing enzymes, 4 M guanidine thiocyanate and Proteinase K, and boiled in 6 M HCl. The isolated melanin can be extensively dialyzed against deionized water, dried and stored at −20° C.

IgG antibodies against melanoma melanin can be produced by hybridoma technology. Mice will be immunized with purified melanin. The melanin can be used with or without adjuvant. Freund's complete adjuvant for initial immunization followed by Freund's incomplete adjuvant can be used. CpG (unmethylated cytosine-guanine dinucleotides) has been shown to be a highly effective (enhances T cell help) and safe immunogen (42). CpG will be used according to the manufacturer's recommendations (ImmunoEasy Mouse Adjuvant, Qiagen). Priming with heat-killed MNT1 melanoma cells followed by boosting with the protein can also be used. Although the intraperitoneal approach has been used in the immunizations that identified mAb 6D2 to *C. neoformans* melanin (23), the base of tail route appears to be a more effective route since the lymph nodes in this region drain directly into the peritoneal lymph nodes that are rich in dendritic cells, which are considered to be the first line of antigen presentation (43). Serum will be obtained prior to immunization and at various times following immunization. Effectiveness of immunization can be determined by incubation of serially diluted serum in 96 well plates coated with melanin that has been blocked for non-specific binding. Following incubation of the serum, the wells will be washed and alkaline phosphatase (AP)-labeled goat anti-mouse (GAM) IgG/M will be applied. The reaction will be developed with p-nitrophenyl phosphate substrate (p-NPP) and measured at an OD of 405 nm. Pre-immune serum will be compared to serum obtained after immunization for each mouse. For responder mice, the isotypes of the mAbs will be characterized using the ELISA with specific immunoglobulin isotypes.

Splenocytes from mice with strong antibody responses to immunization will be fused with non-producing myeloma partners (23). Hybridomas will be generated by a fusion of spleen cells to myeloma cells at a 4:1 ratio in the presence of 50% polyethyleneglycol. The cell mixture will be suspended in a defined complete hypoxanthine-aminopterin-thymidine (HAT) media, with L-glutamine containing 20% heat-inactivated fetal bovine serum, 10% NCTC-109, HAT, and 1% nonessential amino acids for selection of hybridomas, plated in 96-well tissue culture plates, and incubated in a 10% $CO_2$ incubator at 37° C. Screening of the hybridomas for the presence of mAbs to the melanin antigen will be performed by incubation of supernatants in 96 well plates coated with immunogen then blocked to prevent non-specific binding. The wells will be washed and AP-labeled (GAM) IgG/M will be applied. The reaction will be developed with p-NPP and measured at an OD of 405 nm. The isotypes of the mAbs will be characterized. Large volumes of supernatant will be generated from the selected hybridomas, purified by a column of agarose beads labeled with Ab to the appropriate mouse immunoglobulin (Sigma), and concentrated by centrifugation in an 100,000 NMWL Ultrafree®-15 centrifugal filter device (Millipore).

Generation of anti-melanoma melanin IgG F(ab')$_2$ and Fab' fragments. F(ab')$_2$ fragments can be obtained by use of a commercial kit (ImmunoPure, Pierce) as in (44). Briefly, pepsin digestion of IgG at pH 4.2 will be performed, after which the proteolysis will be stopped by centrifugation of the pepsin beads and by adjusting pH to 7 with 5 M sodium acetate. Fab' fragments can be generated by incubation of F(ab')$_2$ fragments with 10 mM dithiothreitol followed by 22 mM iodoacetamide to block the thiol groups. The molecular weight of the obtained fragments can be analyzed by sodium dodecyl sulfate-polyacrylamide gel electrophoresis (SDS-PAGE) and by size-exclusion HPLC. The protein concentration can be determined by the method of Lowry (45).

Derivatization (conjugation) of anti-melanin antibody and antibody fragments with bifunctional chelating agents. In order to radiolabel an antibody with a radiometal, it is necessary to conjugate a bifunctional chelating agent to the antibody prior to radiolabeling. The choice of radioisotopes to perform quality control of radiolabeled antibodies or in vivo imaging studies is ruled by the concept of "matching pairs" of radiopharmaceuticals. This concept calls for the use of diagnostic isotopes (no α- or α-particles emissions) for imaging procedures and quality control with chemistries similar to those of therapeutic isotopes (46). 111-Indium ($^{111}$In) which is readily available commercially is a substitute for therapeutic isotope $^{213}$Bi (46) because of their shared similar chemical properties. Consequently, these isotopes can be used for labeling under identical conditions, and their biodistribution properties are very similar. Hence, the immunoreactivity and, further on, biodistribution results obtained with $^{111}$In are readily applicable to $^{213}$Bi.

For radiolabeling with $^{188}$Re, antibodies and F(ab')$_2$ and Fab' fragments will be derivatized with succinimidyl-HYNIC (hydrazynonicotinamide) and purified as in (47). The advantage of employing "indirect" labeling via bifunctional chelating agents such as HYNIC or others over "direct" labeling is that the radiolabeling process is greatly simplified and shortened by using the aliquots of HYNIC-antibody which can be stored frozen for prolonged periods of time. The incorporation of HYNIC into the proteins will be monitored spectrophotometrically at 385 nm (48). The initial HYNIC to protein ratio will be chosen so that the final HYNIC to protein ratio does not exceed ~1.5 since above this number a partial loss of mAb's immunoreactivity may occur.

For radiolabeling with $^{213}$Bi or $^{111}$In, antibodies and F(ab')$_2$ and Fab' fragments will be conjugated to N-[2-amino-3-(p-isothiocyanatophenyl)propyl]-trans-cyclohexane-1,2-diamine-N,N',N", N''',N''''-pentaacetic acid (CHXA") as in (49) with average number of chelates per antibody of ~1.5 as will be determined by the Yttrium-Arsenazo III. spectrophotometric method (50).

Synthesis of tumoral melanin-binding peptides modified at N terminus with biotin for immunofluorescence, CHXA" and HYNIC ligands for radiolabeling. Fungal melanin-binding peptides have been previously identified and sequenced from the phage display library (24). Tumoral melanin-binding peptides will be identified using the same technique and can be synthesized with biotin, CHXA" and HYNIC ligands at the N terminus. The structures of the peptides will be verified by mass spectrometry and amino acid sequencing.

Immunoreactivity determination. The immunoreactivity of generated F(ab')$_2$ and Fab' fragments, as well as HYNIC- and CHXA"-derivatized 6D2, whole IgG, its fragments and derivatized 4B4 peptide will be determined by melanoma melanin ELISA as described in (40) and confirmed by immunofluorescence as in (51).

5. Discussion

The present application demonstrates that it is possible to radiolabel an anti-melanin antibody with a variety of isotopes without a loss of immunoreactivity. In addition, the application demonstrates that radiolabeled anti-melanin mAb binds to pigmented melanoma cells and that the binding is directly proportional to the degree of melanization of the cells. Hence, the labeled antibody will localize to a melanoma in a subject. Further, animals xenografted with pigmented human melanoma cells were successfully imaged with $^{99m}$Tc-6D2 and treated with $^{188}$Re-6D2 mAb and with $^{188}$Re-HYNIC-D-4B4. Hence, administration of radiolabeled anti-melanin antibody translates into a therapeutic effect.

Figure 10:
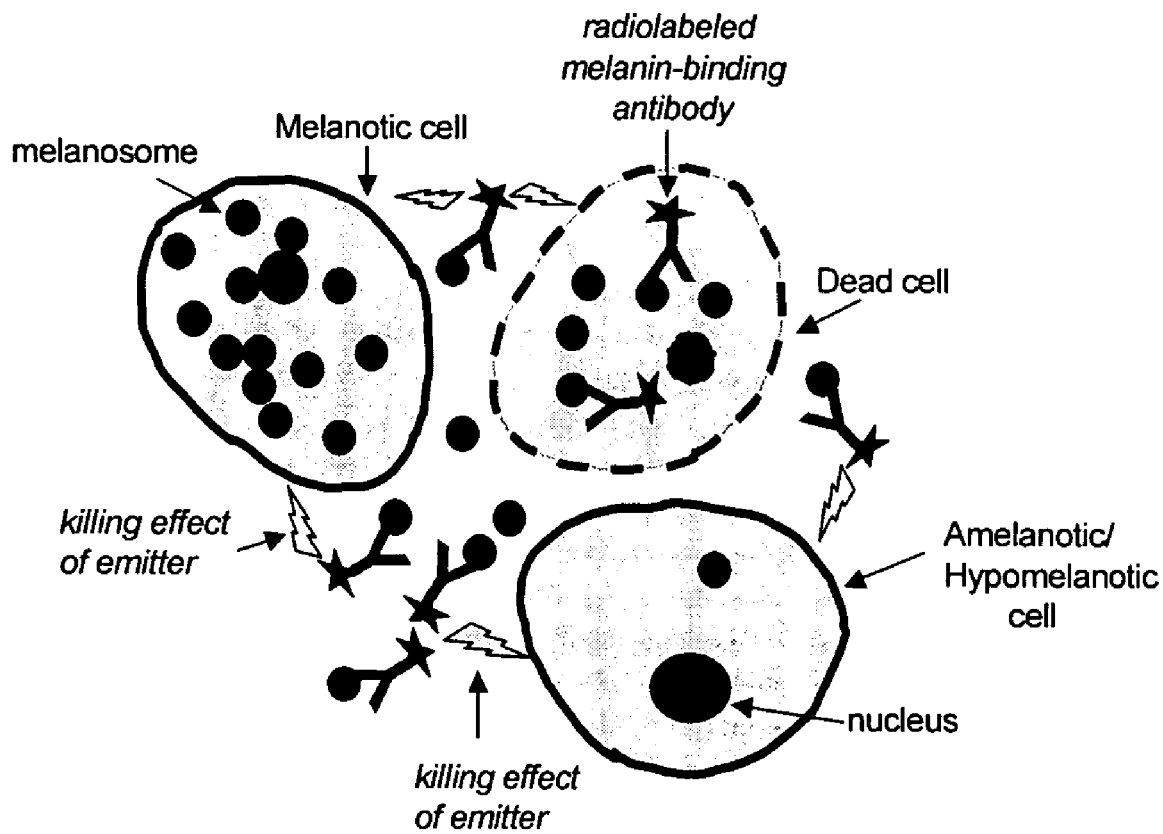
FIG. 10. Schematic of the conceptual approach to radiotherapy by anti-melanin mAb. Melanin is released from melanoma cells as a consequence of cell turnover. Anti-melanin antibody binds to free melanin and delivers cytotoxic radiation to the area. Melanized, weakly melanized and amelanotic cells are killed by radiation through "cross-fire" effect.

The RIT approach described herein is useful against melanotic melanomas which constitute the majority of melanomas. It can also be useful against amelanotic melanomas which are generally hypomelanotic (i.e., have small amounts of melanin) rather than truly amelanotic and produce tyrosinase which demonstrates that they can synthesize melanin (61, 62). Targeting melanin with anti-melanin radiolabeled antibodies should not select for the evolution of a melanotic melanoma into an amelanotic tumor since amelanotic variants in a normal tumor would still be susceptible to killing by the "cross-fire" effect of radiation emanating from the radiolabeled antibody bound to melanin in the tumor mass (FIG. 10).

No uptake of $^{188}$Re-6D2 antibody was observed in the melanised skin on the tails, in the hair follicles, eyes, or in the brains on scintigraphic images of back C57BL/6 mice, which was confirmed histologically by the absence of radiation damage to these tissues. Thus, antibody therapy targeting melanin in patients should not harm non-malignant melanized cells such as normal melanocytes or melanin-containing neurons since melanin in healthy tissue can be expected to be intracellular and not accessible to antibody.

The RIT approach described herein should also be useful for treating tumors using a radiolabeled antibody that binds to a cellular component released by a dying tumor cell. This techniques is particularly useful for treatment of aggressive, rapidly growing tumors where the cell turnover is much higher than in normal, healthy tissue.

REFERENCES

1. Rigel D S Malignant melanoma: incidence issues and their effect on diagnosis and therapy in the 1990s. Mayo Clin. Proc., 72: 367-371, 1997.
2. Grin-Jorgensen C M, Rigel D S and Friedman R J The world-wide incidence of malignant melanoma. In: C. M. Balch, A. N. Houghton, G. W. Milton, A. J. Sober, and S. J. Soong (eds.), Cutaneous Melanoma, Ed. 2, pp. 27-39. Philadelphia: J. B. Lippincott Co., 1992.
3. Liu T and Soong S J Epidemiology of malignant melanoma. Surg. Clin. N. Am., 76: 1205-1222, 1996.
4. Sun W, Schuchter L M. Metastatic melanoma. Curr Treat Options Oncol 2: 193-202, 2001.
5. Safa M M and Foon K A Adjuvant immunotherapy for melanoma and colorectal cancers, Semin. Oncol. 28: 68-92, 2001.
6. Kang N V and Yong A. New techniques for imaging metastatic melanoma. Surgery (St. Louis), 16: v-vii, 1998.
7. Larson S M, Carrasquillo J A, Krohn K A Localization of 131-I-labeled p97-specific Fab fragments in human melanoma as a basis for radiotherapy. J. Clin. Invest. 72: 2101-2114, 1983.
8. Goldenberg, D. M. (ed.) Cancer therapy with radiolabeled antibodies. CRC Press, Boca Raton, Fla., 1995.
9. Knox, S J, Meredith, R F. Clinical radioimmunotherapy. Semin. Radiat. Oncol. 10: 73-93, 2000.
10. Satyamoorthy K, Chehab N H, Waterman M J, Lien M C, El-Deiry W S, Herlyn M, Halazonetis T D. Aberrant regu- 10. lation and function of wild-type p53 in radioresistant melanoma cells. Cell Growth Differ 11: 467-474, 2000.
11. Jenrette J M. Malignant melanoma: the role of radiation therapy revisited. Semin. Oncol. 23: 759-762, 1996.
12. Murtha A D: Review of low-dose-rate radiobiology for clinicians, Semin. Radiation Oncol., 10: 133-138, 2000.
13. Knox S J, Goris M L, Wessels B W. Overview of animal studies comparing radioimmunotherapy with dose equivalent external beam radiation. Radiother. Oncol. 23: 111-117, 1992.
14. Lindmo T, Boven E, Mitchell J B, Morstyn G, Bunn P A Jr. Specific killing of human melanoma cells by 125I-labeled 9.2.27 monoclonal antibody. Cancer Res. 45: 5080-5087, 1985.
15. Charlton D E. The survival of monolayers of cells growing in clusters irradiated by 211 At appended to the cell surfaces. Radiat Res. 151: 750-753, 1999.
16. Ong G L, Elsamra S E, Goldenberg D M, Mattes M J. Single-cell cytotoxicity with radiolabeled antibodies. Clin Cancer Res 7: 192-201, 2001.
17. Kwok C S, Crivici A, MacGregor W D, Unger M W. Optimization of radioimmunotherapy using human malignant melanoma multicell spheroids as a model. Cancer Res. 49: 3276-3281, 1989.
18. Allen B J, Rizvi S M, Tian Z. Preclinical targeted alpha therapy for subcutaneous melanoma. Melanoma Res 11: 175-182, 2001.
19. Larson S M, Carrasquillo J A, McGuffin R W, Krohn K A, Ferens J M, Hill L D, Beaumier P L, Reynolds J C, Hellstrom K E, Hellstrom I. Use of I-131 labeled, murine Fab against a high molecular weight antigen of human melanoma: preliminary experience. Radiology. 155: 487-492, 1985.
20. Kinnaert E, Morandini R, Simon S, Hill H Z, Ghanem G, Van Houtte P. The degree of pigmentation modulates the radiosensitivity of human melanoma cells. Radiat Res. 154: 497-502, 2000.
21. Hill, H Z The function of melanin or six blind people examine an elephant. Bioessays 14: 49-56, 1992.
22. Rofstad, E K Radiation biology of malignant melanoma. Acta Radiol. Oncol. 25: 1-10, 1986.
23. Rosas A L, Nosanchuk J D, Feldmesser M, Cox G M, McDade H C, Casadevall A. Synthesis of polymerized melanin by *Cryptococcus neoformans* in infected rodents. Infect Immun. 68: 2845-2853, 2000.
24. Nosanchuk J D, Valadon P, Feldmesser M, Casadevall A. Melanization of *Cryptococcus neoformans* in murine infection. Mol Cell Biol. 19: 745-750, 1999.
25. Nosanchuk J D, Casadevall A. Cellular charge of *Cryptococcus neoformans*: contributions from the capsular polysaccharide, melanin, and monoclonal antibody binding. Infect. Immun. 65: 1836-1841, 1997.
26. Blower P J, Clark K, Link E M. Radioiodinated methylene blue for melanoma targeting: chemical character-risation and tumour selectivity of labeled components. Nucl Med Biol 24: 305-310, 1997.
27. Kushimoto T, Basrur V, Valencia J, Matsunaga J, Vieira W D, Ferrans V J, Muller J, Appella E, Hearing V J. A model for melanosome biogenesis based on the purification and analysis of early melanosomes. Proc Natl Acad Sci USA. 98: 10698-10703, 2001.
28. Mogensen C E, Soiling K. Studies on renal tubular protein reabsorption: partial and near complete inhibition by certain amino acids. Scand J Clin Lab Invest. 37: 477-486, 1977.
29. Bernard B F, Krenning E P, Breeman W A, Rolleman E J, Bakker W H, Visser T J, Macke H, de Jong M. D-lysine reduction of indium-111 octreotide and yttrium-90 octreotide renal uptake. J Nucl Med. 38: 1929-1933, 1997.
30. Behr T M, Behe M, Kluge G, Gotthardt M, Schipper M L, Gratz S, Arnold R, Becker W, Goldenberg D M. Nephrotoxicity versus anti-tumour efficacy in radiopeptide therapy: facts and myths about the Scylla and Charybdis. Eur J Nucl Med Mol Imaging. 29: 277-279, 2002.
31. Knapp, F. F. Jr. Rhenium-188—a generator-derived radioisotope for cancer therapy. Cancer Biother Radiopharm. 13: 337-349, 1998.
32. Hoher M., Wohrle J, Wohlfrom M, Hanke H, Voisard R, Osterhues, H H, Kochs M, Reske S N, Hombach V, Kotzerke J. Intracoronary beta-irradiation with a liquid 188-Re-filled balloon: six-month results from a clinical safety and feasibility study. Circulation 101: 2355-2360, 2000.
33. Palmedo H, Guhlke S, Bender H, Sartor J, Schoeneich G, Risse J, Grunwald F, Knapp F. F. Jr, Biersack H J. Dose escalation study with rhenium-188 hydroxyethylidene diphosphonate in prostate cancer patients with osseous metastases. Eur. J. Nucl. Med. 27: 123-130, 2000.
34. McDevitt M R, Barendswaard E, Ma, D, Lai L, Curcio M J, Sgouros G, Ballangrud A M, Yang W H, Finn R D, Pellegrini V. An alpha-particle emitting antibody [213Bi] J591 for radioimmunotherapy of prostate cancer. Cancer Res. 60: 6095-6100, 2000.
35. Kennel S J, and Mirzadeh S. Vascular targeted radioimmunotherapy with 213-Bi—an alpha-particle emitter. Nucl. Med. Biol. 25: 241-246, 1998.
36. Behr T M, Behe M, Stabin M G, Wehrmann E, Apostolidis C, Molinet R, Strutz F, Fayyazi A, Wieland E, Gratz S. High-linear energy transfer (LET) alpha versus low-LET beta emitters in radioimmunotherapy of solid tumors: therapeutic efficacy and dose-limiting toxicity of 213Bi-versus 90Y-labeled CO17-1A Fab' fragments in human colonic cancer model. Cancer Res. 59: 2635-2643, 1999.
37. Adams G P, Shaller C S, Horak E M, Simmons H H, Dadachova K, Chappell L L, Wu C, Marks J D, Brechbiel M W and Weiner L M. Radio-immunotherapy of established solid tumor xenografts with alpha and beta emitter-conjugated anti-HER2/neu single-chain Fv (scFv) and diabody molecules. Cancer Biother. Radiopharm. 15:402a. (Abstr.), 2000.
38. Kolbert K S, Hamacher K A, Jurcic J G, Scheinberg D A, Larson S M, Sgouros G. Parametric images of antibody pharmacokinetics in 213Bi-HuM195 therapy of leukimia. J. Nucl. Med. 42: 27-32, 2001.
39. Sgouros G, Ballangrud A M, Jurcic J G, McDevitt M R, Humm J L, Erdi Y E, Mehta B M, Finn R D, Larson S M and Scheinberg D A. Pharmacokinetics and dosimetry of an alpha-particle emitter labeled antibody: 213Bi-HuM195 (anti-CD33) in patients with leukemia. J. Nucl. Med. 40: 1935-1946. 1999.
40. Rosas A L, Nosanchuk J D, Gomez B L, Edens W A, Henson J M, Casadevall A. Isolation and serological analyses of fungal melanins. J Immunol Methods 244: 69-80, 2000.
41. Krieg A M Immune effects and mechanisms of action of CpG motifs. Vaccine 19: 618-622, 2000.
42. Weeratna R D, McCluskie M J, Xu Y, and Davis H L CpG DNA induces stronger immune responses with less toxicity than other adjuvants. Vaccine 18:1755-1762, 2000.

43. Lelouard, H., E. Gatti, F. Cappello, O. Gresser, V. Camosseto, and P. Pierre. Transient aggregation of ubiquitinated proteins during dendritic cell maturation. Nature 517: 177-182, 2002.
44. Lendvai N, Casadevall A, Liang Z, Goldman D L, Mukherjee J, Zuckier L. Effect of immune mechanisms on the pharmacokinetics and organ distribution of cryptococcal polysaccharide. J Infect Dis. 177: 1647-1659, 1998.
45. Lowry O H, Rosebrough N J, Farr A L, and Randall R J. Protein measurement with the Folin phenol reagent. J. Biol. Chem. 193: 265-275, 1951.
46. Mirzadeh S, Brechbiel M W, Atcher R W, Gansow O A. Radiometal labeling of immunoproteins: covalent linkage of 2-(4-isothiocyanatobenzyl)diethylenetriamine-pentaacetic acid ligands to immunoglobulin. Bioconjug. Chem. 1: 59-65, 1990.
47. Blankenberg F G, Katsikis P D, Tait J F, Davis R E, Naumovski L, Ohtsuki K, Kopiwoda S, Abrams M J, Strauss H W. Imaging of apoptosis (programmed cell death) with 99 mTc annexin V. J Nucl Med. 40: 184-191, 1999.
48. King T P, Zhao S W, Lam T Preparation of protein conjugates via intermolecular hydrazone linkage. Biochem. 25: 5774-5779, 1986.
56. Buchsbaum, D. J. 2000. Experimental radioimmunotherapy. *Semin. Radiat. Oncol.* 10: 156-167.
57. Saha G B Fundamentals of Nuclear Pharmacy, Springer, 1997, New York, pp. 139-143
58. Paganelli G., Zoboli S., Cremonesi M. et al Receptor-mediated radionuclide therapy with 90-Y-DOTA-D-Phe-Tyr$^3$-Octreotide: Preliminary report in cancer patients. Cancer Biother. Radiopharm. 14: 477-483, 1999.
59. Early P. J. and Sodee D. B. Principles and Practice of Nuclear Medicine, Mosby, 1995.
60. Abbas A K, Lichtman A H, Pober J S. Cellular and Molecular Immunology, $4^{th}$ edition, W.B. Saunders Co., Philadelphia, 2000.
61. Busam K J, Hester K, Charles C, Sachs D L, Antonescu C R, Gonzalez S, Halpern A C. Detection of clinically amelanotic malignant melanoma and assessment of its margins by in vivo confocal scanning laser microscopy. Arch Dermatol 2001 July; 137(7):923-9.
62. Cohen-Solal K A, Crespo-Carbone S M, Namkoong J, Mackason K R, Roberts K G, Reuhl K R, Chen S. Progressive appearance of pigmentation in amelanotic melanoma lesions. Pigment Cell Res 2002 August; 15(4):282-9.
63. Virgolini I, Traub T, Novotny C, Leimer M, Fuger B, Li S R, Patri P, Pangerl T, Angelberger P, Raderer M, Andreae F, Kurtaran A, Dudczak R. New trends in peptide receptor radioligands. Q J Nucl Med. 2001 45(2):153-159.

SEQUENCE LISTING

<160> NUMBER OF SEQ ID NOS: 1

<210> SEQ ID NO 1
<211> LENGTH: 10
<212> TYPE: PRT
<213> ORGANISM: Bacteriophage fd-tet

<400> SEQUENCE: 1

Tyr Glu Arg Lys Phe Trp His Gly Arg His
1               5                   10

49. Dadachova E, Mirzadeh S, Smith S V, Knapp F F, and Hetherington E L Radiolabelling antibodies with 166-Holmium. Appl. Rad. Isotop. 48: 477-481, 1997.
50. Pippin C G, Parker T A, McMurry T J, and Brechbiel M W. Spectrophotometric method for the determination of a bifunctional DTPA ligand in DTPA-monoclonal antibody conjugates. Bioconjug. Chem. 3: 342-345, 1992.
51. Nosanchuk J D, Rosas A L, and Casadevall A. The antibody response to fungal melanin in mice, J. Immunol. 1998, 160: 6026-6031.
52. Boll R A, Mirzadeh S, and Kennel S J. Optimizations of radiolabeling of immunoproteins with 213-Bi. Radiochim. Acta 79: 145-149, 1997.
53. Abrams M J, Juweid M, tenKate C I, Schwartz D A, Hauser M M, Gaul F E, Fuccello A J, Rubin R H, Strauss H W, Fischman A J. Technetium-99m-human polyclonal IgG radiolabeled via the hydrazino nicotinamide derivative for imaging focal sites of infection in rats. J. Nucl. Med. 31: 2022-2028, 1990.
54. Dadachova E, Mirzadeh S. The role of tin in the direct labelling of proteins with Rhenium-188. Nucl. Med. Biol. 24: 605-608, 1997.
55. Milenic, D. E. 2000. Radioimmunotherapy: designer molecules to potentiate effective therapy. *Semin. Radiat. Oncol.* 10: 139-155.

What is claimed is:

1. A method of treating a subject having a melanin-containing tumor which comprises administering to the subject a radiolabeled monoclonal antibody that specifically binds to melanin, wherein the radiolabeled monoclonal antibody is administered in a radiation dose of 1-1000 mCi and wherein administration of the radiolabeled monoclonal antibody to the subject inhibits growth of the melanin-containing tumor.

2. A method of imaging a melanin-containing tumor in a subject which comprises administering to the subject an amount of a radiolabeled monoclonal antibody effective to image the tumor, wherein the radiolabeled monoclonal antibody specifically binds to melanin and wherein the radiolabeled monoclonal antibody binds to melanin from a dead or dying melanin-containing tumor cell.

3. A method for treating a melanin-containing melanoma in a subject which comprises administering to the subject an amount of a radiolabeled monoclonal antibody effective to treat the melanoma, wherein the radiolabeled monoclonal antibody specifically binds to melanin.

4. A method for imaging a melanin-containing melanoma in a subject which comprises administering to the subject an amount of a radiolabeled monoclonal antibody effective to image the melanoma, wherein the radiolabeled monoclonal antibody specifically binds to melanin.

5. The method of claim 1 or 3 wherein the antibody is labeled with an alpha-emitting radioisotope.

6. The method of claim 5 wherein the alpha-emitting radioisotope is 213-Bismuth.

7. The method of claim 1 or 3 wherein the antibody is labeled with a beta-emitting radioisotope.

8. The method of claim 7 wherein the beta-emitting radioisotope is 188-Rhenium.

9. The method of claim 1 or 3 wherein the antibody is labeled with a radioisotope selected from the group consisting of a positron emitter and an admixture of any of an alpha emitter, a beta emitter, and a positron emitter.

10. The method of claim 2 or 4 wherein the antibody is labeled with a radioisotope selected from the group consisting of a beta emitter, a positron emitter, and an admixture of a beta emitter and a positron emitter.

11. The method of claim 2 or 4 wherein the antibody is labeled with a radioisotope selected from the group consisting of 99m-Technetium, 111-Indium, 67-Gallium, 123-Iodine, 124-Iodine, 131-Iodine and 18-Fluorine.

12. The method of claim 1, 2, 3 or 4 wherein the subject is a mammal.

13. The method of claim 12 wherein the mammal is a human.

14. The method of claim 3 wherein the amount effective to treat the melanoma is a dose of 1-1000 mCi.

15. The method of claim 1, 2, 3 or 4, wherein the antibody is a F(ab')₂ fragment or a Fab' fragment of a whole antibody.

16. The method of claim 1, 2, 3 or 4, wherein the antibody is an IgM antibody, an IgG antibody, or an IgA antibody.

17. The method of claim 1, 2, 3 or 4, wherein uptake of radiolabeled antibody by the kidney is inhibited by administering a positively charged amino acid to the subject.

18. The method of claim 17, wherein the amino acid is D-lysine.

19. The method of claim 1 or 3 which further comprises administering to the subject an amount of antibodies radiolabeled with a plurality of different radioisotopes.

20. The method of claim 19, wherein the radioisotopes are isotopes of a plurality of different elements.

21. The method of claim 19, wherein at least one radioisotope is a long range emitter and at least one radioisotope is a short range emitter.

22. The method of claim 21, wherein the long-range emitter is a beta emitter and the short range emitter is an alpha emitter.

23. The method of claim 22, wherein the beta emitter is 188-Rhenium and the alpha emitter is 213-Bismuth.

24. The method of claim 19, wherein the plurality of different radioisotopes is more effective in treating the tumor than a single radioisotope within the plurality of different radioisotopes, where the radiation dose of the single radioisotope is the same as the combined radiation dose of the plurality of different radioisotopes.

25. The method of claim 3 or 4, wherein uptake of the radiolabeled monoclonal antibody in the melanoma is at least 10 times greater than in surrounding muscle.

26. The method of claim 3 or 4, wherein the radiolabeled monoclonal antibody is not taken up by non-cancerous melanin-containing tissue.

27. The method of claim 26, wherein the non-cancerous melanin-containing tissue is hair, eyes, skin, brain, spinal cord, and/or peripheral neurons.

28. The method of claim 1 or 3, which comprises multiple administrations of the radiolabeled antibody to the subject.

29. The method of claim 1, 3 or 4, wherein where the radiolabeled monoclonal antibody binds to melanin from a dead or dying melanoma cell.

30. The method of claim 3, wherein administration of the radiolabeled monoclonal antibody to the subject inhibits growth of the melanoma.

31. The method of claim 1, wherein administration of the radiolabeled monoclonal antibody to the subject decreases the volume of the melanin-containing tumor.

32. The method of claim 3, wherein administration of the radiolabeled monoclonal antibody to the subject decreases the volume of the melanoma.

* * * * *

UNITED STATES PATENT AND TRADEMARK OFFICE
CERTIFICATE OF CORRECTION

| | | |
|---|---|---|
| PATENT NO. | : 7,402,385 B2 | Page 1 of 1 |
| APPLICATION NO. | : 10/775869 | |
| DATED | : July 22, 2008 | |
| INVENTOR(S) | : Ekaterina Dadachova et al. | |

It is certified that error appears in the above-identified patent and that said Letters Patent is hereby corrected as shown below:

In the Specification

Column 1, lines 11-17, should read:

-- STATEMENT OF GOVERNMENT SUPPORT

This invention was made with government support under grant number AI001489 awarded by the National Institutes of Health. The government has certain rights in the invention. --

Signed and Sealed this
Fifteenth Day of December, 2015

Michelle K. Lee
*Director of the United States Patent and Trademark Office*